United States Patent
Evans et al.

(10) Patent No.: US 9,314,507 B2
(45) Date of Patent: Apr. 19, 2016

(54) METHODS OF TREATMENT OF HEART FAILURE WITH NATRIURETIC PEPTIDES

(75) Inventors: Daron Evans, San Mateo, CA (US); Hsiao Lieu, Burlingame, CA (US); William P. Van Antwerp, Valencia, CA (US)

(73) Assignee: Capricor Therapeutics, INC., Beverly Hills, CA (US)

( * ) Notice: Subject to any disclaimer, the term of this patent is extended or adjusted under 35 U.S.C. 154(b) by 0 days.

(21) Appl. No.: 13/284,529

(22) Filed: Oct. 28, 2011

(65) Prior Publication Data

US 2012/0178689 A1    Jul. 12, 2012

Related U.S. Application Data

(60) Provisional application No. 61/408,320, filed on Oct. 29, 2010, provisional application No. 61/440,154, filed on Feb. 7, 2011.

(51) Int. Cl.
- *A61P 9/04* (2006.01)
- *A61K 38/22* (2006.01)
- *C07K 14/575* (2006.01)
- *C07K 14/58* (2006.01)

(52) U.S. Cl.
CPC ............. *A61K 38/2242* (2013.01); *A61K 38/22* (2013.01); *C07K 14/575* (2013.01); *C07K 14/58* (2013.01)

(58) Field of Classification Search
None
See application file for complete search history.

(56) References Cited

U.S. PATENT DOCUMENTS

2005/0113286 A1    5/2005   Schreiner et al.

FOREIGN PATENT DOCUMENTS

WO    WO 03/079979 A2    10/2003

OTHER PUBLICATIONS

Evans, Nile Therapeutic Press Release dated Oct. 14, 2008; 3 pages as printed.*
O. Lisy et al., Design Synthesis, and Actions of a Novel Chimeric Natriuretic Peptide: CD-NP, Journal of American College of Cardiology, vol. 52, No. 1, pp. 60-68, 2008.
H. G. Riter et al., "Nonhypotensive Low-Dose Nesiritide has Differential Renal Effects Compared with Standard-Dose Nesiritide in Patients with Acute Decompensated Heart Failure and Renal Dysfunction." Journal of the American College of Cardiology, vol. 47, No. 11, pp. 2334-2335, Jun. 2006.
E. S. Chung et al., "Safety and Tolerability of Serial Home Infusions of Nesiritide for Advanced Heart Failure." American Journal of Cardiology, vol. 97, No. 9, pp. 1370-1373, May 1, 2006.
H. Lieu et al., "Initial Observations of Intravenous CD-NP, Chimeric Natriuretic Peptide, on Renal Functions in Chronic Heart Failure Patients." Journal of Cardial Failure, vol. 15, No. 6, p. S77, Aug. 1, 2009.
International Preliminary Report on Patentability dated Apr. 30, 2013.

* cited by examiner

*Primary Examiner* — Zachary Howard
(74) *Attorney, Agent, or Firm* — Knowles Intellectual Property Strategies; Brent R. Bellows

(57) ABSTRACT

Methods of treating heart failure, or decreasing blood pressure, comprising administering an NP at an appropriate dose, or in an amount sufficient to provide particular concentrations of NP, are provided.

8 Claims, 16 Drawing Sheets

|  | PL | 1.25 | 2.5 | 3.75 |
|---|---|---|---|---|
| ALL CAUSE MORTALITY | 0 | 0 | 1 (UROSEPSIS) | 0 |
| REHOSP. FOR ACUTE HF | 1 | 1 | 2 | 0 |
| SBP ≤ 95 DURING INFUSION | 1/16 | 0/20 | 2/20 | 4/10 |
| AE TERM FOR HYPOTENSION | 0 | 1 | 0* | 3/10 |
| OCCURRENCE OF SERUM Cr INCREASE > 0.3 mg/dL DURING INFUSION | 4/16 (25%) | 3/20 (15%) | 3/20 (15%) | 3/10 (30%) |
| OCCURRENCE OF SERUM Cr DECREASE > 0.3 mg/dL DURING INFUSION | 0/16 | 7/20 (35%) | 3/20 (15%) | 1/10 (10%) |

FIG. 9

|  | USED IN TRIAL | | | | |
|---|---|---|---|---|---|
|  |  |  |  |  |  |
|  | TARGET: 500 pg/mL | | |  |  |
| WEIGHT RANGE | | DOSE ESTIMATE | | PROJECTED PK | DELTA DOSE |
| 45 | 55 | 10.00 | ug/hr | 480 | 10 |
| 55 | 65 | 12.50 | ug/hr | 490 | 7.5 |
| 65 | 75 | 15.00 | ug/hr | 500 | 5 |
| 75 | 85 | 17.50 | ug/hr | 510 | 2.5 |
| 85 | 95 | 20.00 | ug/hr | 520 | 0 |
| 95 | 105 | 22.50 | ug/hr | 530 | -2.5 |
| 105 | 115 | 25.00 | ug/hr | 540 | -5 |
| 115 | 125 | 27.50 | ug/hr | 550 | -7.5 |
| 125 | 135 | 30.00 | ug/hr | 560 | -10 |
| 135 | 145 | 32.50 | ug/hr | 570 | -12.5 |
| 145 | 155 | 35.00 | ug/hr | 580 | -15 |

FIG. 13

METHODS OF TREATMENT OF HEART FAILURE WITH NATRIURETIC PEPTIDES

CROSS-REFERENCE TO RELATED APPLICATIONS

This application claims the benefit of U.S. Provisional Application 61/408,320 filed on Oct. 29, 2010, which is hereby incorporated by reference in its entirety, and claims the benefit of U.S. Provisional Application 61/440,154 filed on Feb. 7, 2011, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Dec. 19, 2011, is named N78507P7.txt and is 9,159 bytes in size.

BACKGROUND

Heart failure may be chronic or acute. Chronic heart failure may involve a decrease in heart function over time. In this situation, a chronic heart failure patient may suffer from acute heart failure. Acute heart failure may also have other causes, such as trauma or disease. One type of acute heart failure, acute decompensated heart failure ("ADHF"), may be a cause of acute respiratory distress. Current methods for treating heart failure using conventional drugs seek to reduce elevated cardiac filling pressures and increase renal excretion of sodium and water. However, current methods have serious shortcomings. Particularly, when reducing elevated cardiac filling pressures, current methods fail to maintain adequate systemic blood pressure. Thus, current methods may cause a patient to experience potentially dangerous hypotension. In addition, when increasing renal excretion of sodium and water, current methods may cause a decrease in renal function or renal failure.

SUMMARY

In one aspect, methods of treating heart failure, or lowering blood pressure, in a patient by administering natriuretic peptides are provided. In another aspect, methods of administering natriuretic peptides with reduced incidents of hypotension are also provided.

BRIEF DESCRIPTION OF THE DRAWINGS

FIG. 9 is a chart depicting data from an exemplary pilot human clinical study.

FIG. 13 is a chart depicting data from an exemplary weight-based human clinical study.

DETAILED DESCRIPTION

Figure 1:
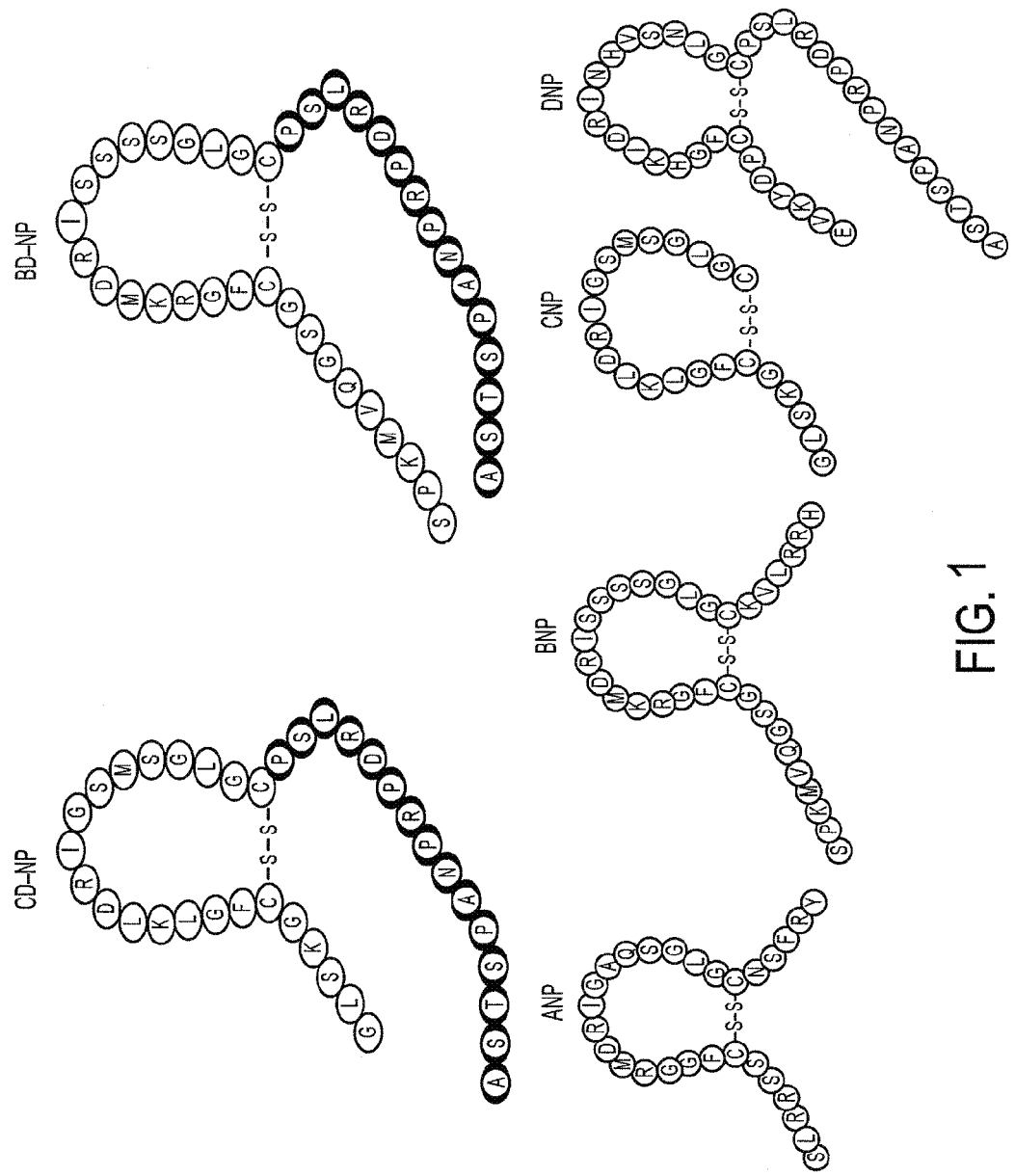
FIG. 1 is a drawing showing the structure of representative NPs (CD-NP (SEQ ID NO. 2), BD-NP (SEQ ID NO. 1), ANP (SEQ ID NO. 5), BNP (SEQ ID NO. 6), CNP (SEQ ID NO. 9), and DNP (SEQ ID NO. 10)).

A natiuretic peptide (NP) may be obtained by any method known in the art. Such methods are described in, for example, Lisy, Ondrej et al., Design, Synthesis, and Actions of a Novel Chimeric Natriuretic Peptide: CD-NP, J. Am. Coll. Cardiol. 52(1) 60-68 (2008) (the entirety of which is hereby incorporated by reference), and U.S. Pat. No. 6,407,211 (the entirety of which is hereby incorporated by reference).

In one aspect, a natriuretic peptide (NP) may be an agonist of natriuretic peptide receptor A (NPRA). In another aspect, an NP may be an agonist of natriuretic peptide receptor B (NPRB). In yet another aspect, an NP may be an agonist of a glucocorticoid receptor (GCR). In a further aspect, an NP may have the sequence of SEQ ID NO.: 2. In an additional aspect, an NP may be a polypeptide. In still another aspect, an NP may increase the production of cyclic guanosine monophosphate (cGMP) in the body. Without wishing to be bound by theory, cGMP is thought to have multiple clinial effects, including a) blood vessel wall relaxation and potential blood pressure reduction, b) increased natriuresis through direct action on kidney tubules, c) prevention of cardiac fibroblast proliferation and d) lusitropic effect on the heart.

Examples of NP's include cenderitide (CD-NP), atrial natriuretic peptide (ANP), brain natriuretic peptide (BNP), C-type natriuretic peptide (CNP), BD-NP, urodilatin, and CU-NP. CD-NP, a representative NP, possesses the ring structure of C-type natriuretic peptide (CNP) and the C-terminus of Dendroaspis natriuretic peptide (DNP). See, for example, U.S. Pat. No. 6,407,211 (the entirety of which is hereby incorporated by reference) at FIGS. 1, 4B, and 4C and the description and explanation of those Figures.

An NP can be, for example, an isolated and purified peptide fragment of Dendroaspis natriuretic peptide (SEQ ID NO:10), wherein the N-terminus of the peptide fragment does not include the sequence Glu-Val-Lys-Tyr-Asp-Pro-Cys-Phe-Gly-His-Lys-Ile-Asp-Arg-Ile-Asn-His-Val-Ser-Asn-Leu-Gly (SEQ ID NO:12), and wherein said peptide fragment has a biological activity selected from the group consisting of vasodilation, natriuresis diuresis and renin suppression.

An NP can be administered in a pharmaceutically acceptable delivery vehicle including, but not limit to, solution, suspension, syrup, powder, tablet, capsule, implant, patch, gel, or implant.

An NP could also be, for example, a peptide compound of the formula (H)-Pro-Ser-Leu-Arg-Asp-Pro-Arg-Pro-Asn-Ala-Pro-Ser-Thr-Ser-Ala-(R) (SEQ ID NO:3), wherein R is OH, $NH_2$, $NHR^3$ or $N(R^3)(R^4)$, wherein $R^3$ and $R^4$ are independently phenyl or $(C_1-C_4)$alkyl; or a pharmaceutically acceptable salt thereof; a peptide compound of the formula (H)-Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Leu-Gly-Cys-Pro-Ser-Leu-Arg-Asp-Pro-Arg-Pro-Asn- Ala-Pro-Ser-Thr-Ser-Ala-(R) (SEQ ID NO:1), wherein R is OH, $NH_2$, NHR$^3$ or N(R$^3$)(R$^4$), wherein R$^3$ and R$^4$ are independently phenyl or (C$_1$-C$_4$)alkyl; wherein the two Cys residues are connected by a disulfide bond; or a pharmaceutically acceptable salt thereof; and/or a peptide compound of the formula: (H)-Gly-Leu-Ser-Lys-Gly-Cys-Phe-Gly-Leu-Lys-Asp-Arg-Ile-Gly-Ser-Met-Ser-Gly-Leu-Gly-Cys-Pro-Ser-Leu-Arg-Asp-Pro-Arg-Pro-Asn-Ala-Pro-Ser- Thr-Ser-Ala-(R) (SEQ ID NO:2), wherein R is OH, NH$_2$, NHR$^3$ or N(R$^3$)(R$^4$), wherein R$^3$ and R$^4$ are independently phenyl or (C$_1$-C$_4$)alkyl; wherein the two Cys residues are connected by a disulfide bond; or a pharmaceutically acceptable salt thereof.

An NP could be, for example, a compound of formula (I):

Formula (I)
X$_0$-Pro-X$_1$-A$_5$-A$_1$-A$_3$-Pro-A$_1$-Pro-A$_1$-A$_5$-Pro-X$_1$-X$_1$-X$_1$-A$_4$-X$_2$
(SEQ ID NO: 13)

wherein A$_1$ is Leu, Lys, Arg, His, Orn, Asn or Gln; A$_3$ is Asp or Glu; A$_4$ is Lys, Arg, Orn, Ala, Thr, Asn, or Gln; A$_5$ is Gly, Ala, Val, Met, Leu, Norleucine or Ile; X$_2$ is absent or is a peptide of from 1 to 35 amino acid residues; X$_1$ is Ser or Thr; X$_0$ is absent or is a peptide of from 1 to 35 amino acid residues; wherein X$_0$ is not Glu-Val-Lys-Tyr-Asp-Pro-Cys-Phe-Gly-His-Lys-Ile-Asp-Arg-Ile-Asn-His-Val-Ser-Asn-Leu-Gly-Cys (SEQ ID NO:11); and wherein the compound is not SEQ ID NO:1; wherein X$_0$ could be a peptide of from 1 to 25 amino acid residues, an amino acid sequence from the N-terminus of brain natriuretic peptide (BNP), SEQ ID NO:7, an amino acid sequence from the N-terminus of C-type natriuretic peptide (CNP), or SEQ ID NO:8.

An NP could also be, for example, a compound which comprises a variant of SEQ ID NO:3, wherein the variant has one or more amino acid substitutions selected from the group consisting of Pro to Gly; Ser to Thr; Thr to Ser; Arg to Lys, Gln or Asn; Ala to Val, Ile, or Leu; Leu to Nor, Ile, Val, Met, Ala, or Phe; Asp to Glu; and Asn to Gln, His, Lys or Arg or a compound which comprises a variant of SEQ ID NO:3, wherein the variant has one or more amino acid substitutions selected from the group consisting of Ser to Thr; Thr to Ser; Arg to Lys, Gln or Asn; Ala to Val, Ile, or Leu; Leu to Nor, Ile, Val, Met, Ala, or Phe; Asp to Glu; and Asn to Gln, His, Lys or Arg optionally having a heterologous peptide at the amino-terminus of the variant peptide selected from brain natriuretic peptide, SEQ ID NO: 7, C-type natriuretic peptide, SEQ ID NO:8, and further, optionally, has a biological activity selected from the group consisting of vasodilation, natriuresis, diuresis and renin suppression.

An NP could also, for example, be a compound of Formula (II):

Formula (II)
X$_0$-Pro-X$_1$-A$_5$-A$_1$-A$_3$-Pro-A$_1$-Pro-A$_1$-A$_5$-Pro-X$_1$-X$_1$-X$_1$-A$_4$-X$_2$
(SEQ ID NO: 14)

wherein A$_1$ is Leu, Lys, Arg, His, Orn, Asn or Gln; A$_3$ is Asp or Glu; A$_4$ is Lys, Arg, Orn, Ala, Thr, Asn, or Gln; A$_5$ is Gly, Ala, Val, Met, Leu, Norleucine or Ile; X$_2$ is absent or is a peptide of from 1 to 35 amino acid residues; X$_1$ is Ser or Thr; X$_0$ is absent or is a peptide of from 1 to 35 amino acid residues; wherein X$_0$ is not Glu-Val-Lys-Tyr-Asp-Pro-Cys-Phe-Gly-His-Lys-Ile-Asp-Arg-Ile-Asn-His-Val-Ser-Asn-Leu-Gly-Cys (SEQ ID NO:11); wherein the compound is not SEQ ID NO: 1, and wherein the compound has a biological activity selected from the group consisting of vasodilation, natriuresis, diuresis and renin suppression, wherein X$_0$ could be, for example, a peptide of from 1 to 25 amino acid residues, an amino acid sequence from the N-terminus of brain natriuretic peptide (BNP), SEQ ID NO:7, an amino acid sequence from the N-terminus of C-type natriuetic peptide (CNP), SEQ ID NO:8.

An NP could also be, for example, a natriuretic polypeptide comprising the sequence of amino acids 24-34 of SEQ ID NO:10, wherein the polypeptide further comprises a disulfide ring structure; wherein the polypeptide does not have the sequence set forth in SEQ ID NO: 1; and wherein the polypeptide or fragment thereof has a biological activity selected from the group consisting of vasodilation, natriuresis, diuresis, and renin suppression, wherein, for example, the disulfide ring structure is at least 17 amino acids in length that comprises, for example, a disulfide bond between cysteine residues at positions 1 and 17 of the disulfide ring, wherein, for example, the disulfide ring structure comprises the amino acid sequence set forth in SEQ ID NO:7 or SEQ ID NO:8.

FIG. 1 shows the structure of representative NPs, which have many similar structural features. For example the representative NP's each have a 17 amino acid loop structure. This AA sequence in the loop is structurally similar among the representative NP's in FIG. 1.

One or more NPs may be used to treat patients with chronic heart failure or acute heart failure, including acute decompensated heart failure (ADHF). The terms "treat" or "treatment," in reference to NPs, including, for example, CD-NP, are defined as prescribing, administering, or providing a medication to beneficially effect or alleviate one or more symptoms associated with a disease or disorder, or one or more underlying causes of a disease or disorder. NPs may reduce elevated cardiac filling pressures while maintaining adequate systemic blood pressure, and also increase the renal excretion rate of sodium and water while preserving or enhancing renal function. In one aspect, in order to reduce cardiac filling pressures, NP's may reduce blood pressure by about 5 to about 10 mm Hg. Animal studies show that NPs can reduce blood pressure so much that they may pose a risk of hypotension. See Lisy, Ondrej et al., Design, Synthesis, and Actions of a Novel Chimeric Natriuretic Peptide: CD-NP, *J. Am. Coll. Cardiol.* 52(1) 60-68 (2008).

In one example, as described herein, CD-NP, a representative NP, was used in clinical trials in order to identify a dose range where CD-NP had a clinical effect without causing undesired hypotension. Similar results could be expected with other NPs because, for example, all NPs may be agonists for the same receptors.

First in Human Clinical Study

In an exemplary human clinical trial with CD-NP (FIH Study, or NIL-CDNP-CT001), CD-NP was dosed in two phases. An open-label, ascending dose phase followed a randomized, double-blind, placebo-controlled dose confirmation phase conducted in 22 healthy subjects to determine the maximum tolerated dose (MTD), and collect preliminary efficacy and safety information. Doses of 10 ng/kg/min, 17.5 ng/kg/min and 25 ng/kg/min were tested in the trial. The MTD was identified as 17.5 ng/kg/min. At 17.5 ng/kg/min, orthostatic hypotension was noted immediately after the infusion in some subjects in both CD-NP and placebo arms, but more events were observed in the CD-NP arm. At 25 ng/kg/min, two out of four subjects experienced symptomatic hypotension in association with orthostatic challenge immediately post-infusion. In the orthostatic challenge, patients were asked to stand quickly while their blood pressure was measured. The test is designed to provide an early signal of a potential hypotension risk.

Figure 2A:
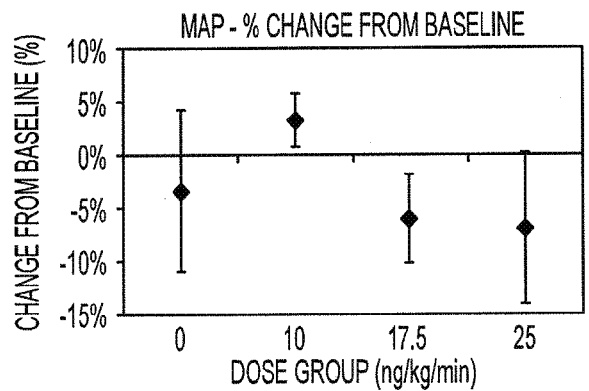
FIG. 2 is a set of graphs depicting data from an exemplary human clinical study.
Figure 2B:
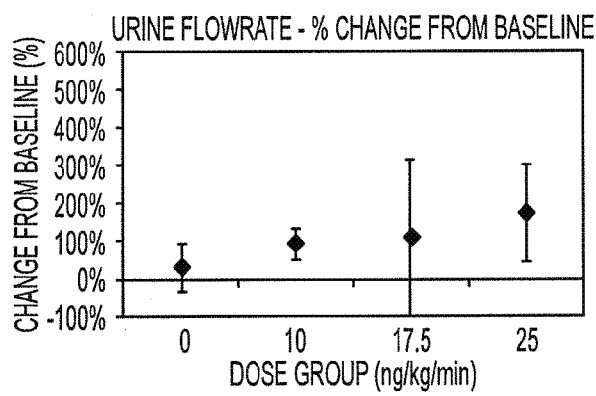
Figure 2C:
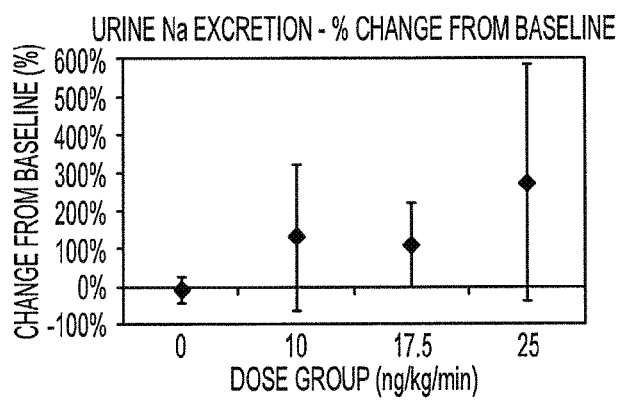

Exemplary results from the FIH study are shown in FIG. 2. Mean arterial pressure (MAP) (equal to [systolic blood pressure+2× diastolic blood pressure]/3) was measured in the trial. As shown in FIG. 2a, a 25 ng/kg/min dose of CD-NP reduced MAP more than treatment with a placebo. The reduction in blood pressure during CD-NP dosing did not induce symptomatic hypotension. However, as shown in FIGS. 2b and 2c, CD-NP demonstrated an increase in natriuresis, and a trend toward an increase in diuresis. CD-NP administration also led to suppression of aldosterone (not shown). In one aspect, suppression of aldosterone may be correlated to lower mortality rates in heart failure patients. In another aspect, suppression of aldosterone may be correlated to improved renal function, for example, increases in diuresis or natriuresis. Pharmacokinetic data showed that a steady state of natriuretic peptide was achieved within 1-2 hours, and the terminal elimination half-life was approximately 15-20 minutes. Cyclic guanosine monophosphate (cGMP), a secondary messenger of the natriuretic peptide receptor, was shown to increase in the plasma in a dose dependent manner.

Based on the results of this exemplary study, it was determined that a dose of about 17.5 ng/kg/min would likely be safe and tolerable in heart failure patients, and that a dose of about 25 ng/kg/min could potentially cause hypotension.

Maximum Tolerated Dose Clinical Study

Another exemplary clinical study of CD-NP was an open-label, ascending dose clinical study in 20 stable heart failure patients (MTD Study, or NIL-CDNP-CT002). During Day 0 of the study, patients were on their normal medication, furosemide (commonly known as Lasix®, a registered trademark of Sanofi-Aventis Deutschland GMBH Corporation). On Day 1 of the study, diuretic and vasoactive medications were withheld and CD-NP was administered to the patients for 24 hours.

Figure 3A:
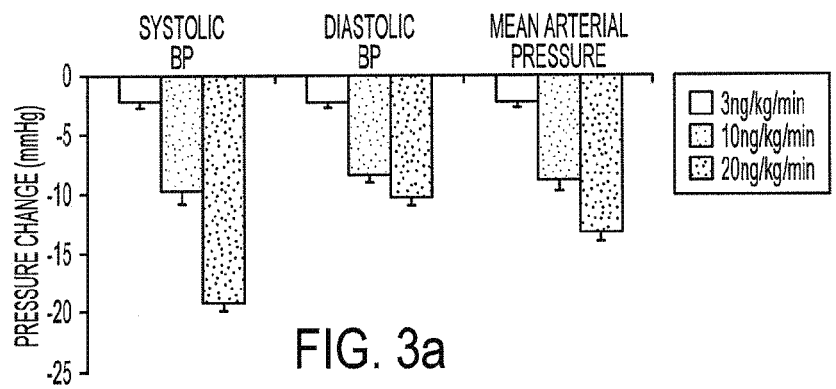
FIG. 3 is a set of graphs depicting data from an exemplary maximum tolerated dose human clinical study.
Figure 3B:
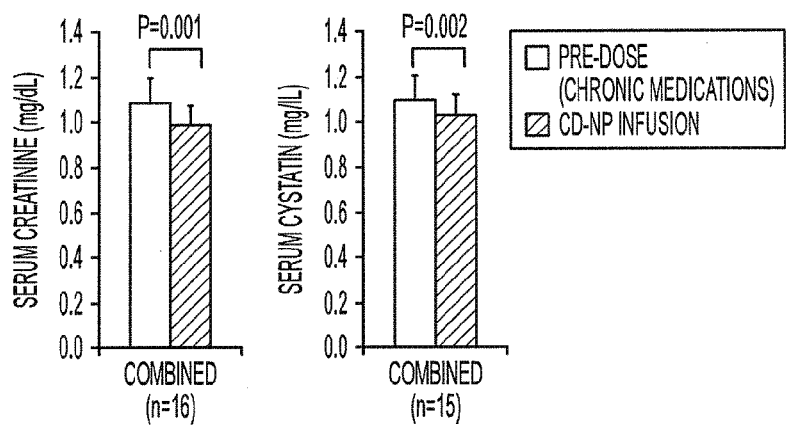
Figure 3C:
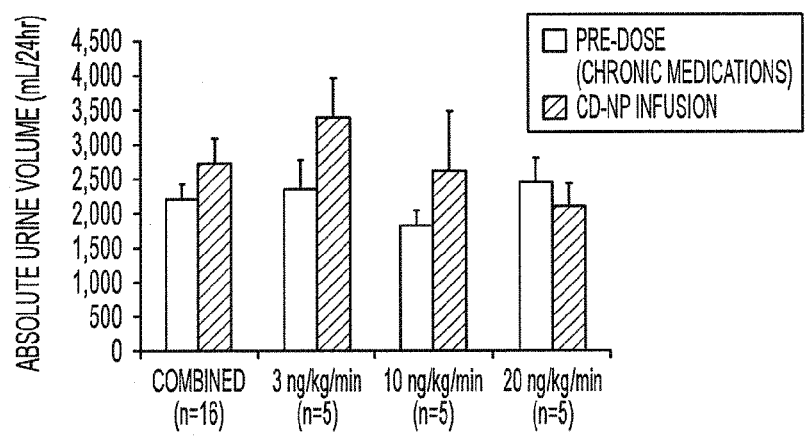

Exemplary results of this study are shown in FIG. 3. As depicted in FIG. 3c, patients had increased absolute urine volume after administration of CD-NP, indicating increased diuresis. As depicted in FIG. 3b, patients also showed increased renal function, as measured by a reduction in serum creatine (which relates to an increase in creatinine clearance) and cystatin-C, after their medication was switched from furosemide to CD-NP. These results were achieved at doses of CD-NP between 3 ng/kg/min and 20 ng/kg/min. A 24-hour infusion at doses ranging from 3 ng/kg/min to 20 ng/kg/min was tolerated and an exemplary maximum tolerated dose was identified as about 20 ng/kg/min. Dose escalation was limited by the occurrence of symptomatic hypotension in 2 of 2 patients who received 30 ng/kg/min infusions of CD-NP. In addition, an episode of asymptomatic hypotension occurred at 10 ng/kg/min and an episode of symptomatic hypotension occurred at 20 ng/kg/min of CD-NP. All events were reported as mild or moderate and resolved within 2 hours. IV fluid was administered in one patient who received the 30 ng/kg/min dose.

In this exemplary study, CD-NP caused a dose dependent drop in blood pressure. Placebo was not administered, however each patient's drug response was compared to the patient's baseline measured during Day 0 of the study (i.e., prior to administration of CD-NP). FIG. 3a shows blood pressure drop change in patients dosed at 3 ng/kg/min, 10 ng/kg/min, and 20 ng/kg/min after their medication was switched from furosemide to CD-NP. The 3 ng/kg/min dose produced an reduction in systolic blood pressure (SBP) of less than 3 mm Hg. The 10 ng/kg/min dose produced a clinically meaningful reduction in blood pressure. In one aspect, the 20 ng/kg/min dose produced a drop in blood pressure that could result in symptomatic hypotension if a patient was given CD-NP and had starting SPB of less than 120 mm Hg, or less than 110 mmHg, or less than 100 mm Hg, or less than 90 mm Hg. Thus, in another aspect, administering CD-NP to a patient with a starting SPB of greater than 90 mm Hg, or greater than 100 mm Hg, or greater than 110 mm Hg, or greater than 120 mm Hg can be performed without lowering the patient's blood pressure below 90 mm Hg, or below 100 mm Hg, or below 110 mm Hg, or below 120 mm Hg. For example, when the patient is stabilized, or for a chronic heart failure patient, as in this study, the dose can be from about 3 ng/kg/min to about 20 ng/kg/min, or about 5 ng/kg/min to about 20 ng/kg/min, or about 10 ng/kg/min to about 17.5 ng/kg/min.

Hemodynamic Monitoring Clinical Study

Another exemplary study using CD-NP was a multi-center, open-label Phase 2a clinical study of CD-NP in patients hospitalized with acute heart failure requiring hemodynamic monitoring (Hemo Study, or NIL-CDNP-CT003). This study considered the efficacy of 8 hours of intravenous administration of CD-NP on changes in cardiac output and pulmonary capillary wedge pressure (PCWP, or wedge pressure).

Stabilized acute heart failure patients requiring hemodynamic monitoring, and receiving standard-of-care heart failure medications (i.e., furosemide infusion), received an initial 8-hour CD-NP infusion followed by a 14-hour washout period, and then a further 8-hour CD-NP infusion. Hemodynamic measurements were collected for an additional 8 hours and safety measurements were collected for a further 2 days.

Patients were enrolled into one of two sequential cohorts (Cohort A and B) which could include up to 10 evaluable patients in each cohort. Cohort A received 8 hours of 3 ng/kg/min CD-NP, followed by a 14 hour wash-out period, and then 8 hours of 10 ng/kg/min CD-NP. Cohort B received 8 hours of 1 ng/kg/min CD-NP, followed by a 14 hour wash-out period, and then 8 hours of 20 ng/kg/min CD-NP.

Figure 4A:
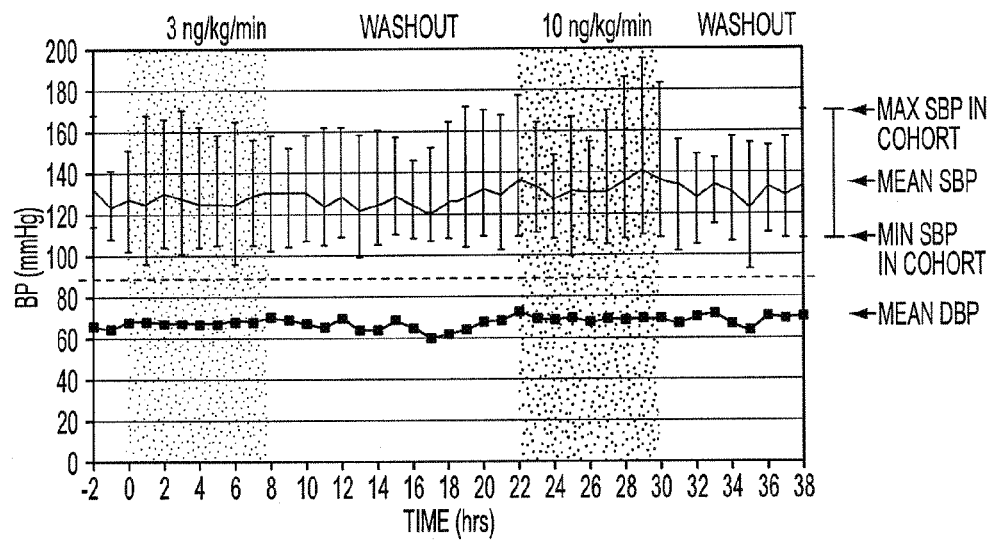
FIG. 4 is a set of graphs depicting data from an exemplary hemodynamic monitoring human clinical study.
Figure 4B:
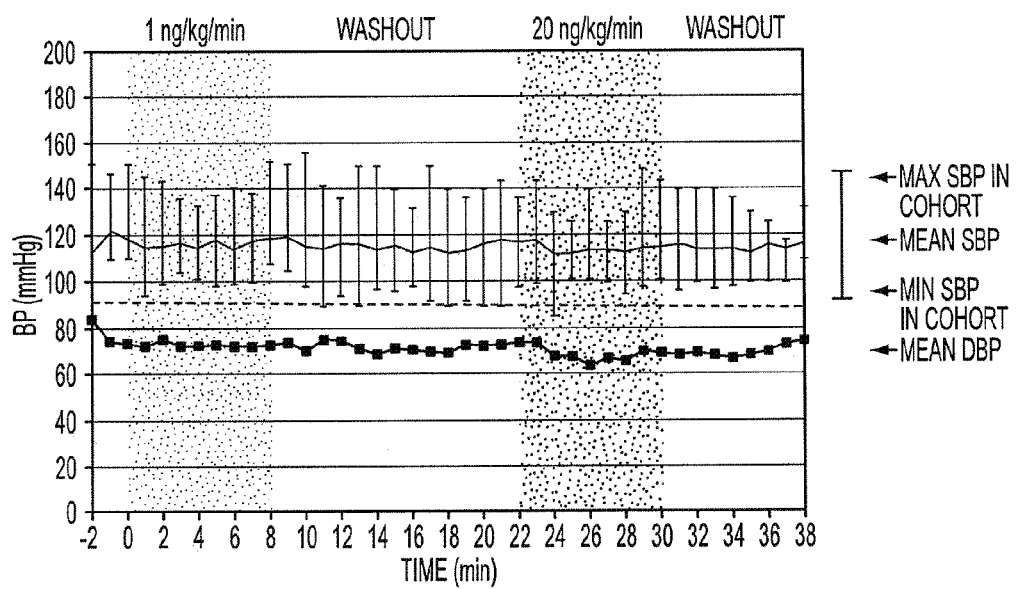

FIG. 4 shows blood pressure data from study patients over the course of a 40 hour treatment cycle. The first 2 hours, (−2 to 0) represent time before administration of CD-NP. Hours 0 to 38 represent time during the CD-NP dosing regimen discussed above. FIG. 4a shows the result for patients dosed at 3 ng/kg/min and 10 ng/kg/min. FIG. 4b shows the result for patients dosed at 1 ng/kg/min and 20 ng/kg/min. These results show that CD-NP administration to stabilized patients had a minimal effect on SBP at doses of 1, 3 and 10 ng/kg/min. At the 20 ng/kg/min dose, one patient had a transient dip in SBP below 90 mmHg, which is the level at which asymptomatic hypotension is triggered.

Figure 5A:
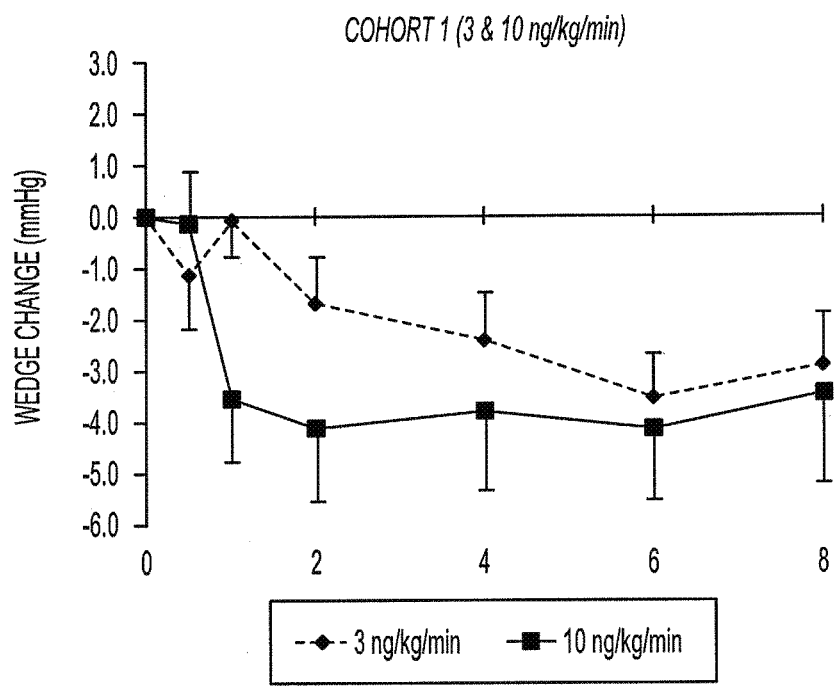
FIG. 5 is a set of graphs depicting data from an exemplary hemodynamic monitoring human clinical study.
Figure 5B:
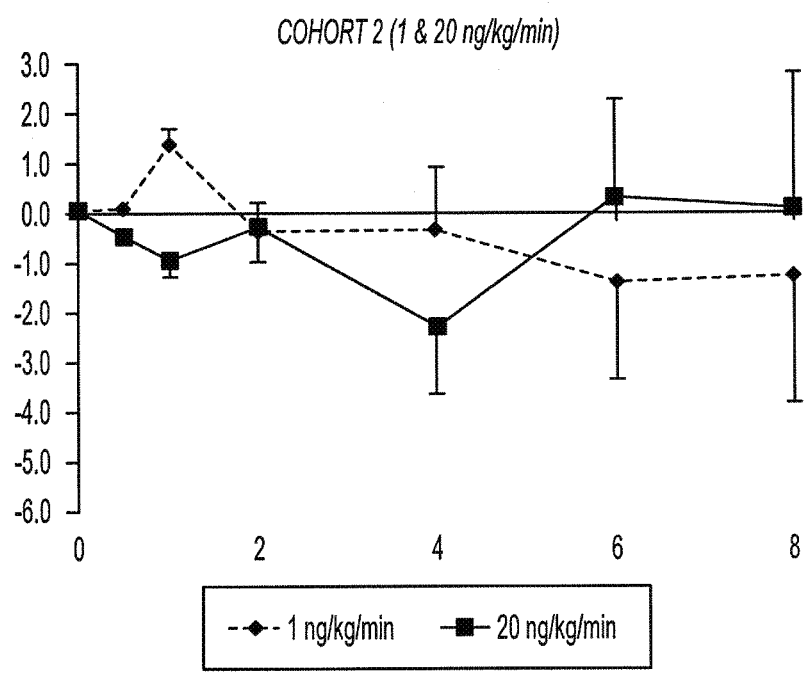

FIG. 5 shows the cardiac benefit of CD-NP administration. FIG. 5a shows that doses of 3 and 10 ng/kg/min appeared to provide a cardiac benefit, as determined by reduction of cardiac filling pressure (wedge change in the Figure). In one aspect, as shown in FIG. 5b, the 1 ng/kg/min dose did not appear to provide any cardiac benefit, because it did not have an effect on cardiac filling pressure. In another aspect, the 20 ng/kg/min dose had a blood pressure effect (FIG. 4b), but as shown in FIG. 5b, no apparent effect on cardiac filling pressure. Thus, in yet another aspect, the cardiac benefit does not continue to increase with increasing dosage of CD-NP.

Figure 6:
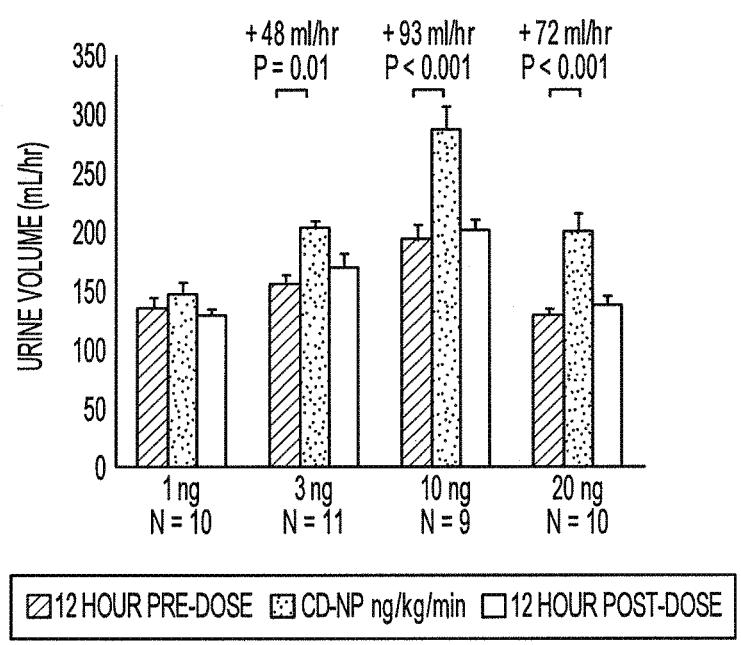
FIG. 6 is a graph depicting data from an exemplary hemodynamic monitoring human clinical study.

FIG. 6 shows the renal benefit of CD-NP administration, as measured by increased urine volume. In a further aspect, when CD-NP is administered at 1 ng/kg/min, the change in urine volume was insignificant Thus, in yet another aspect, administration at 1 ng/kg/min may not produce any renal benefit. As compared to pre-dose urine volume, urine volume of patients dosed at 3 ng/kg/min, increased by 48 mL/hr, and urine volume of patients dosed at 10 ng/kg/min increased by 93 mL/hr. However, patients dosed at 20 ng/kg/min showed an increase in urine volume of only 72 mL/hr. Thus, in another aspect, renal benefit does not continue to increase with increasing dosage.

Surprisingly, the clinical benefit of CD-NP does not continue to increase with increased dosing up to the MDT, nor does the benefit plateau after a threshold level is reached in this exemplary study. Instead, the clinical benefit decreases after a certain threshold that is less than the MDT.

In another aspect, an NP dose range between 3 ng/kg/min and 20 ng/kg/min, or between 3 ng/kg/min and 10 mg/kg/min, or between 3 mg/kg/min and 5 ng/kg/min can be administered to a patient in need of treatment. In another aspect, a dose of about 20 ng/kg/min may indicate a point where the risk of hypotension begins in patients who have a starting SBP of at least 120 mmHg. In yet another aspect, such doses may be safely administered to patients who have a starting SBP of greater than 120 mm Hg. Patients admitted to the hospital, on average, have a starting SBP of 142, with a standard deviation of 32 according to the OPTIMIZE Registry. Only approximately 25% of patients have a starting SBP of less than 120 mmHg. Thus, in a further aspect, a dose up to about 20 ng/kg/min may be appropriate.

CD-NP Dose Selection and Modification

Another exemplary clinical study of CD-NP was a multi-center, open-label, placebo-controlled Phase 2 clinical study of CD-NP in patients hospitalized with acute heart failure with renal dysfunction (Pilot Study, or NIL-CDNP-CT005).

For this study, 5 ng/kg/min of CD-NP was administered to patients for the initial dose. CD-NP dosed at 5 ng/kg/min combined with an IV bolus furosemide dose caused a precipitous drop in blood pressure. Before completion of the treatment period, CD-NP infusion was halted in 2 of 4 patients receiving CD-NP because of symptomatic hypotension. Patient enrollment into the cohort that received 5 mg/kg/min was halted after 4 patients were treated with CD-NP at this dose. The average drop in SBP was 24 mmHg, with a standard deviation of 10 mmHg, as compared to placebo where patients had an average drop in SBP of 13 mmHg, with a standard deviation of 29 mmHg.

In analyzing this result, it should be noted that this study was the first time that CD-NP was dosed in acute heart failure patients within 24 hours of admission. In the Hemo Study, patients were first treated with the standard of care, furosemide infusion, for 1 to 2 days, or 1 day, in order to stabilize the patient. Treatment with furosemide was discontinued before treatment with CD-NP began on day 2-3, or day 2, or day 3, of treatment. When dosed in the first 24 hours upon admission to the hospital, CD-NP was much more potent in acute heart failure patients than expected. In view of the results of the previous studies, this increase in potency was surprising and unexpected.

After analysis of the data, multiple factors potentially contributed to the surprising increased effect of CD-NP in this study. Without being bound by theory, patients admitted to the hospital with heart failure were already taking vasoactive medications such as statins, beta-blockers, oral diuretics, alpha blockers, ACE inhibitor, angiotensin receptor blocker, calcium channel blockers or a combination of the foregoing. Adding CD-NP to a background that includes a vasoactive medication could have a surprisingly synergistic effect with these or other vaseomedications, thus accentuating the effects of CD-NP.

Without being bound by theory, the timing of CD-NP dosing versus the timing of the last IV bolus dose of furosemide (furosemide also being a vasoactive medication) could have had an impact on the effects of CD-NP dosing. This is important, because furosemide is the standard of care for acute heart failure patients. When administered via IV bolus dose, furosemide causes the kidney to quickly excrete fluid, which may leave the patient in an intravascularly fluid depleted state. This state of intravascular fluid depletion dissipates over time, for example from about 2 to about 4 hours, or about 2 hours, or about 3 hours, or about 4 hours, after administration of the furosemide bolus, as fluid from the tissues is absorbed into the blood stream. Without being bound by theory, a more potent vasoactive effect may be observed if one or more NPs are administered during a state of intravascular fluid depletion.

Although, in hindsight, a possible explanation, which is not intended to be binding, has been offered, these results were still surprising. This is because in previous studies, when CD-NP was co-administered with furosemide to stabilized heart failure patients, CD-NP was well tolerated up to 20 ng/kg/min. However, when CD-NP was co-administered with furosemide in the acute hospital setting to acute heart failure patients, the MTD was only at 3.75 ng/kg/min. In one aspect, when CD-NP is co-administered with furosemide, CD-NP unexpectedly and surprisingly exhibits a 5.3 folds increase in relative potency over that in stabilized or chronic heart failure patients.

Without being bound by theory, this unexpected and surprising potency enhancement may relate to a large intravascular volume shift in acute heart failure patients exposed to both CD-NP and an additional vasoactive medication, such as furosemide. Again, without wishing to be bound by theory, it is also possible that there may be an upregulation of natriuretic peptide receptors in acute heart failure patients that is not present in stabilized or chronic heart failure patients (i.e., patients who have already been treated with furosemide).

The Pilot Study was restarted, testing a CD-NP dose level of 1.25 ng/kg/min. After it was confirmed that CD-NP was safe and tolerable at 1.25 ng/kg/min, the dose was escalated to 2.5 ng/kg/min. After safety was confirmed at 2.5 ng/kg/min, the dose level was raised to 3.75 ng/kg/min. At 3.75, there was a signal of blood pressure reduction that could cause symptomatic hypotension. CD-NP was started within 24 hours after admission to the hospital, and CD-NP was administered continuously for 72 hours.

Figure 7A:
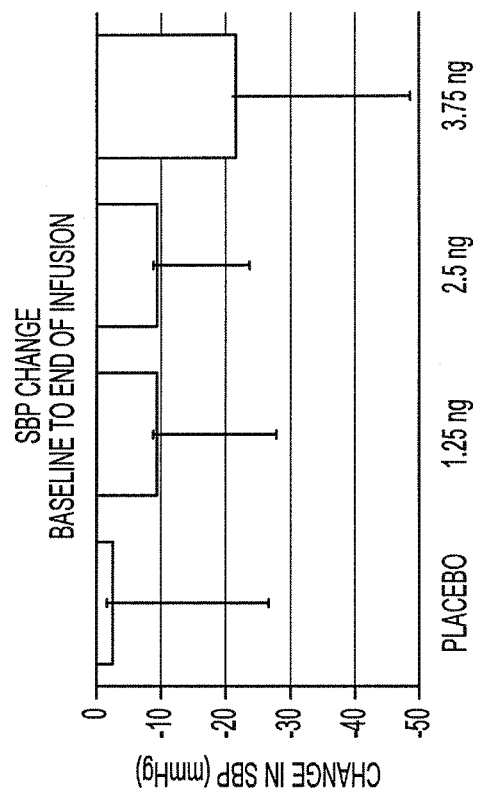
FIG. 7 is a set of graphs depicting data from an exemplary pilot human clinical study.
Figure 7B:
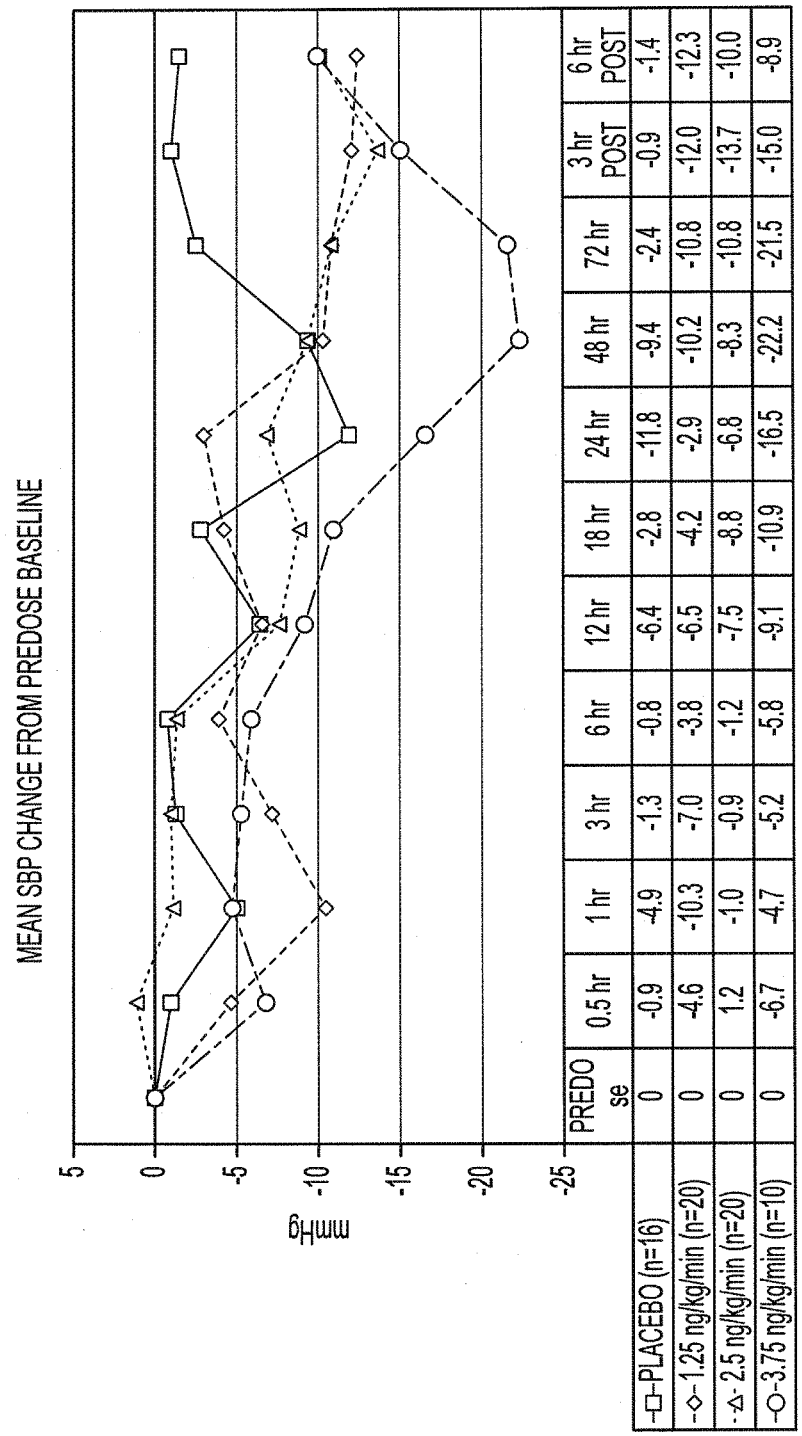

Exemplary results of this study are presented in FIG. 7. FIG. 7a shows the change in SBP from the baseline (before treatment) until the end of the CD-NP infusion. The results presented in FIG. 7a show that dosages as low as 1.25 ng/kg/min provide a clinical benefit, as demonstrated by a lowering of SBP. FIG. 7b shows that a CD-NP dose of 2.5 ng/kg/min may, in some patients, be more desirable than 1.25 ng/kg/min. In particular, SBP increased less rapidly post-infusion after a dose of 2.5 ng/kg/min than after a dose of 1.25 ng/kg/min. While a dose of 3.75 ng/kg/min may bring about some hypotension risk, this dose and higher dosages may still be appropriate for patients whose starting SBP is high.

Figure 8A:
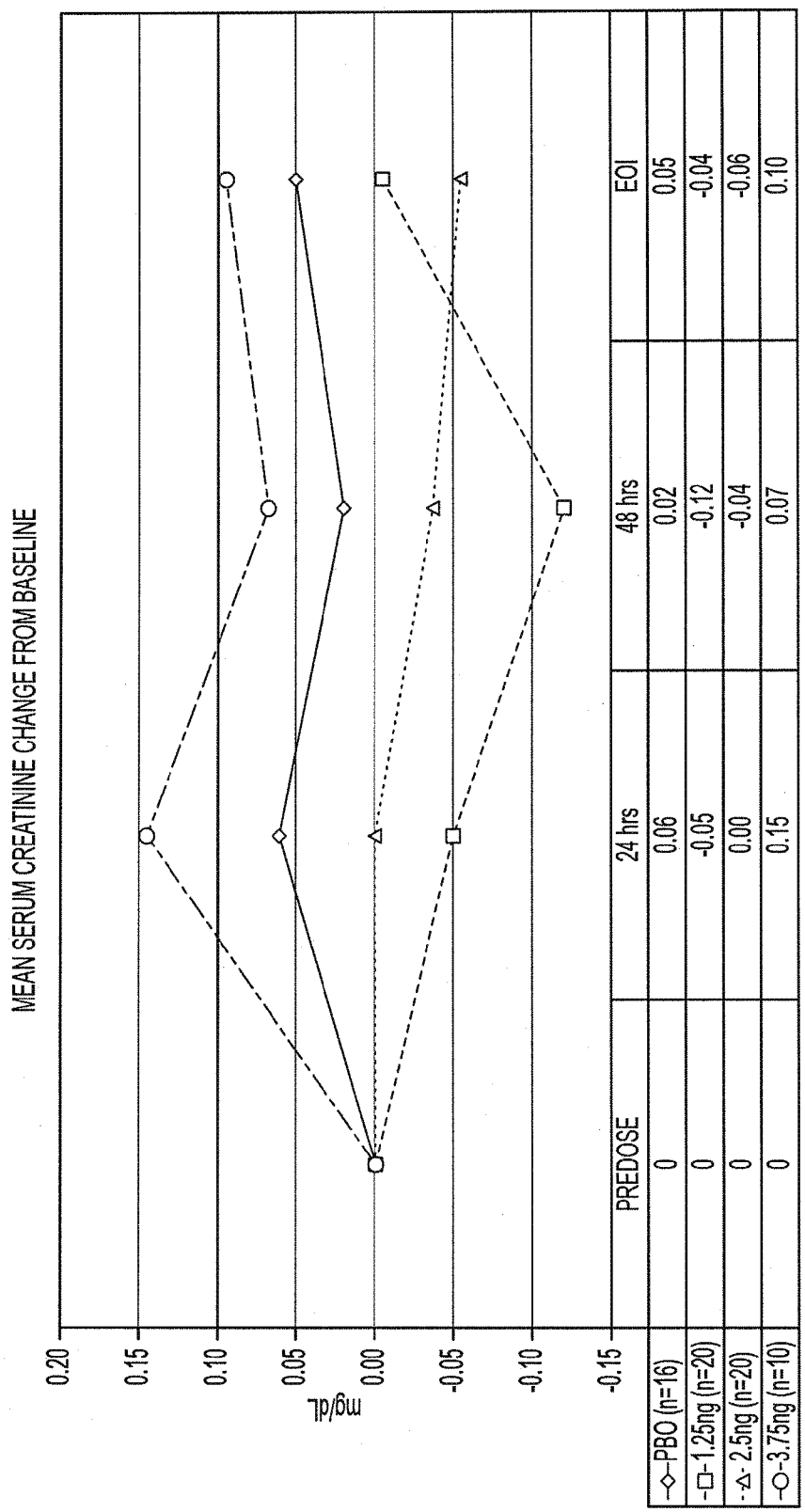
FIG. 8 is a set of graphs depicting data from an exemplary pilot human clinical study.
Figure 8B:
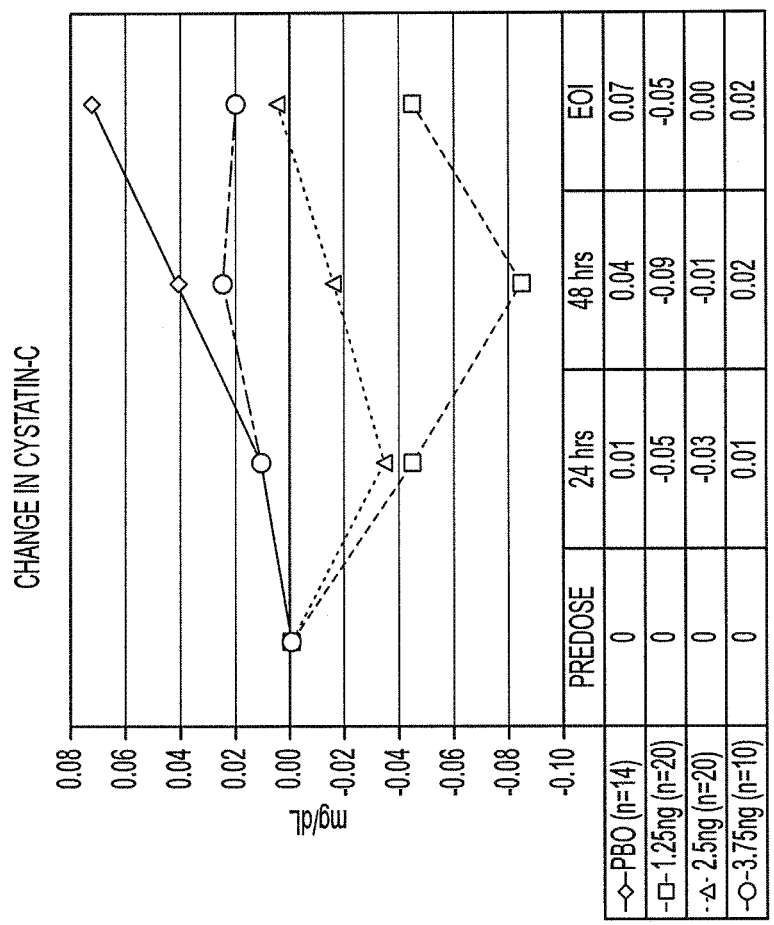

In one aspect, the 3.75 ng/kg/min dose decreased plasma BNP levels versus placebo. Without being bound by theory, a reduction in BNP levels is believed to correlate to a reduction in heart strain and is also believed to correlate with symptomatic improvement of the patient. As shown in FIG. 8, CD-NP administration also provided a renal benefit, as measured by serum creatinine and serum cycstatin-c levels. FIG. 8a shows that creatinine levels increased as compared to a placebo at doses of 1.25 ng/kg/min, 2.5 ng/kg/min, and 3.75 ng/kg/min. Similarly, FIG. 8b shows that cystatine-c levels decreased s compared to a placebo at doses of 1.25 ng/kg/min, 2.5 ng/kg/min, and 3.75 ng/kg/min, as depicted. In this Figure, the change in creatinine and cystatin-c levels were dose-dependant.

Figure 8C:
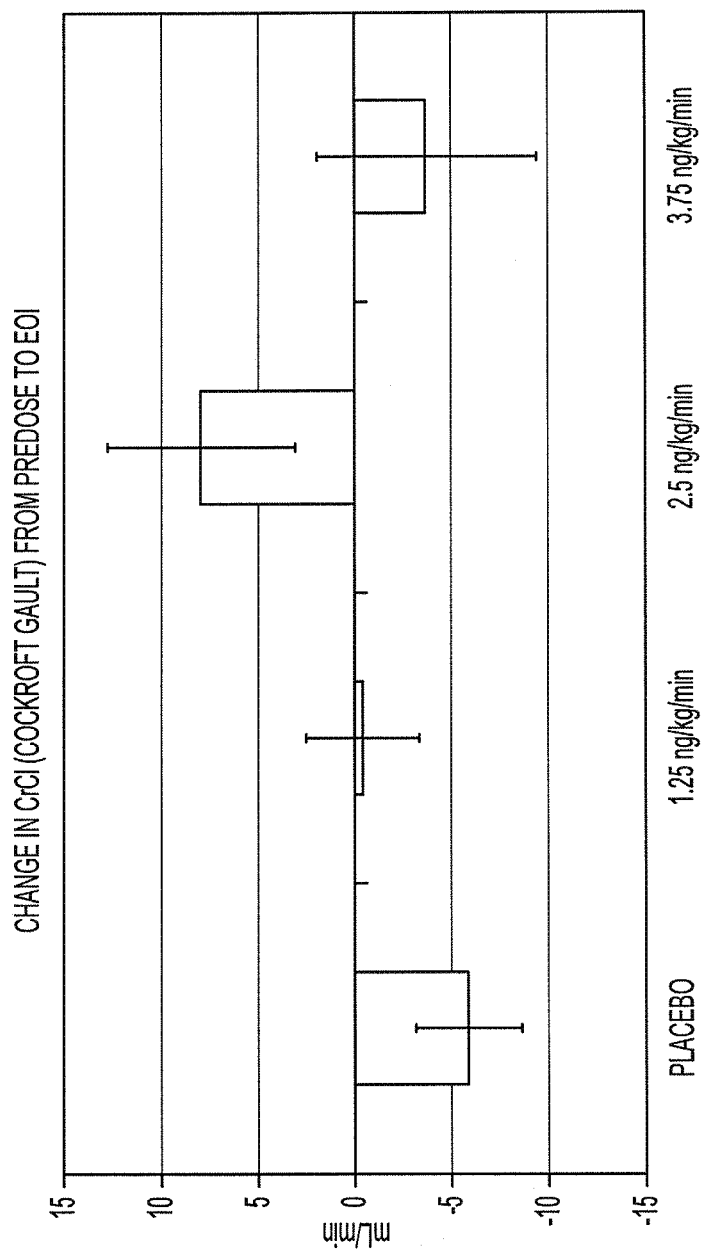

FIG. 8c shows the change in creatinine clearance (CrCl) for patients given a placebo, and patients treated with CD-NP at doses of 1.25 ng/kg/min, 2.5 ng/kg/min, and 3.75 ng/kg/min. As depicted in this Figure, where increased creatinine clearance is used as a surrogate for renal function, the lowest does, 1.25 ng/kg/min, appears not to effect renal function; the 2.5 ng/kg/min dose appears to improve renal function; and the 3.75 ng/kg/min dose appears to decrease renal function. Without being bound by theory, it is believed that, in this aspect, the 1.25 ng/kg/min dose was insufficient to give a renal benefit, the 2.5 ng/kg/min dose afforded renal benefit, and any renal benefit of the 3.75 ng/kg/min dose was confounded by the large drop in blood pressure.

FIG. 9 shows exemplary results, including adverse effects (AE). According to the data depicted in this Figure, one patient in the study died (from urosepsis), and the rate of rehospitalization for acute heart failure (Rehosp. for acute HF) was low. Risk of hypotension, as determined by an SBP of 95 or less, was dose dependant with no hypotension among patients dosed at 1.25 ng/kg/min, two instances (10%) among patients dosed at 2.5 mg/kg/min, and four instances (40%) among patients dosed at 3.75 mg/kg/min. FIG. 9 also shows the incidence of increases and decreases of serum creatinine (serum Cr in the Figure). Several patients on CD-NP (35% for the 1.25 ng/kg/min dose) had decreases of serum creatinine greater than 0.3 mg/dL, which indicates a clinically relevant improvement in kidney function. No patients receiving the placebo showed this benefit. A few patients, mostly those receiving 3.75 mg/kg/min, showed an increase in serum creatinine levels of more than 0.3 mg/dL, which relates to decreased renal function.

FIG. 10 shows additional exemplary clinical results. Notably, the number of patients who experienced hypotension or a SBP drop to 95 mm Hg or less during the study was very low for patients dosed at 1.25 ng/kg/min and 2.5 ng/kg/min.

In another aspect, when co-administered with one or more vasoactive medications, such as furosemide, statins, beta-blockers, oral diuretics, or alpha blockers, or a combination of the foregoing, a CD-NP dose between about 1 ng/kg/min and about 3.75 ng/kg/min, or between about 1.25 ng/kg/min and about 3.5 ng/kg/min, or between about 1.5 ng/kg/min and about 2.5 ng/kg/min, or about 1.25 ng/kg/min or about 2.5 ng/kg/min, or about 3 ng/kg/min, or about 3.75 ng/kg/min may be appropriate. In yet another aspect, although a dose of between 3 and 5 ng/kg/min might increase the risk of hypotension begins in patients who have a starting SBP of at least 120 mm Hg, dosing at this level may still be appropriate for many patients, for example, patients who have a starting SBP of greater 150 mm Hg, or greater than 140 mm Hg, or greater than 130 mm Hg, or greater than 120 mm Hg.

Thus, by administering the appropriate amount of NP, such as CD-NP, blood SBP may be decreased by 3 mm Hg to 20 mm Hg, or by 5 mm Hg to 15 mm Hg, or by 5 mm Hg to 10 mm Hg.

Dosing Study

In a dosing study, CD-NP was administered to patients with chronic heart failure. The amount of CD-NP administered was either a set amount (in µg/hr) regardless of the patient's weight, or was varied based on the patient's weight.

Figure 10A:
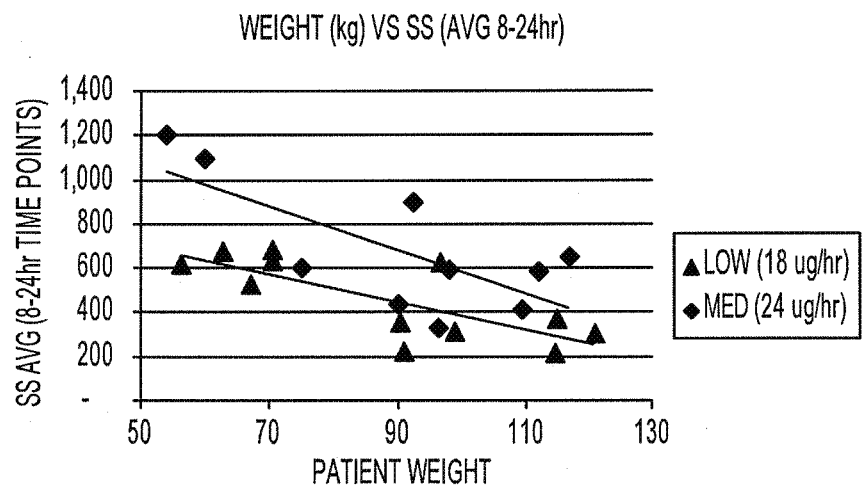
FIG. 10 is a chart depicting data from an exemplary pilot clinical study.
Figure 10B:
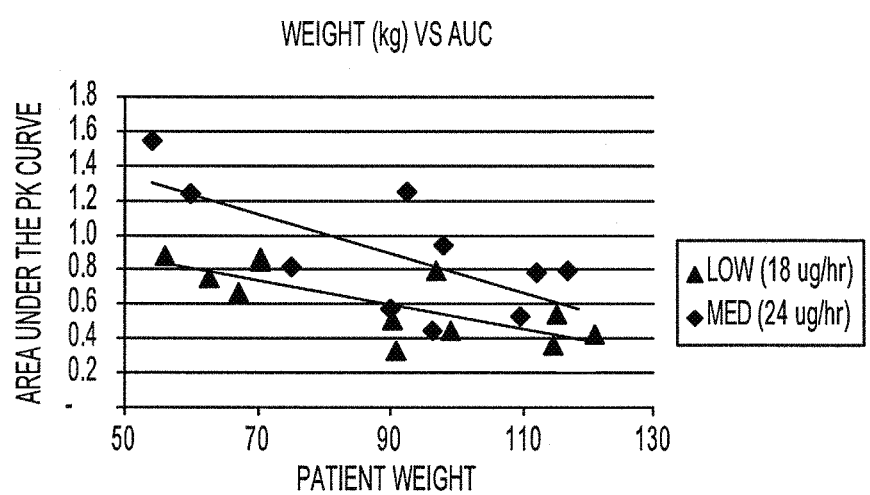

FIG. 10 shows an exemplary relationship between patient weight and pharmacokinetic (PK) data. In FIG. 10a, the steady state average (SS Avg) serum concentration of CD-NP in pg/mL is plotted against patient weight for patients who received low (18 µg/hr) and medium (24 µg/hr) doses of CD-NP. This Figure shows that the serum concentration of CD-NP at either dose decreases with increasing patient weight. Similarly, FIG. 10b shows that the area under the curve (AUC) decreases with increasing patient weight.

Figure 11:
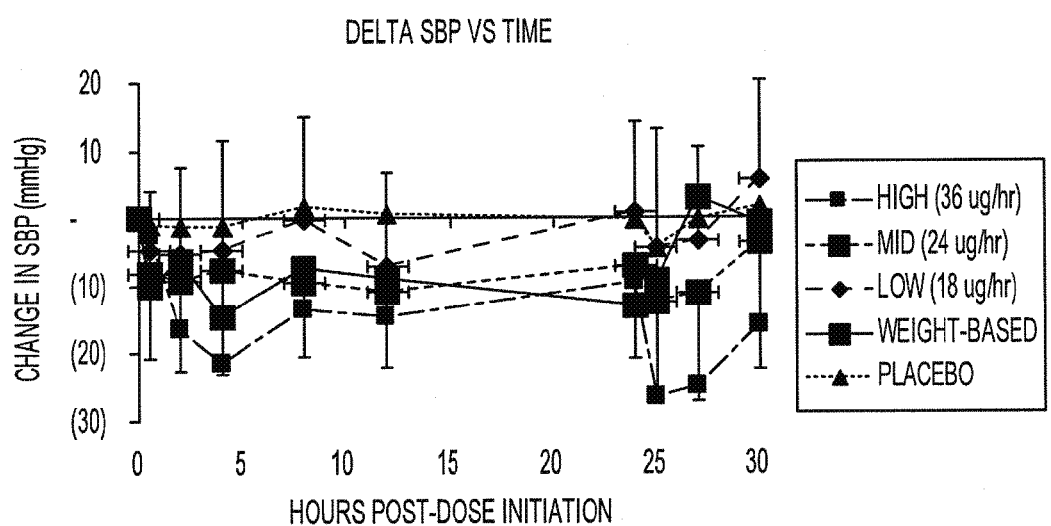
FIG. 11 is a set of graphs depicting data from an exemplary weight-based clinical study.

FIG. 11 shows the cardiac benefit of CD-NP under the conditions of this study, as measured by change in SBP. The placebo group had no significant change in SBP over the course of the study. In this Figure, the low dose group (18 µg/hr, or 300 ng/min) gave only a small change in SBP over the 30 hours after dose initiation. The medium dose group (24 µg/hr, or 400 ng/min) showed a clinically significant decrease in SBP. In one aspect, the SBP decrease for doses 24 µg/hr is insufficient to cause a risk of hypotension. The high dose group (36 µg/hr, or 600 ng/min) showed a decrease in SBP that could possibly cause hypotension in patient's with starting SBP less than 120 mm Hg, or less than 110 mm Hg, or less than 100 mm Hg, or less than 90 mm Hg. The weight-based group received a dose that depended on the patients weight. Using PK data, for example the linear fit of data from FIG. 10a, the dose was adjusted to give a predicted serum concentration of 500 pg/mL.

Figure 12:
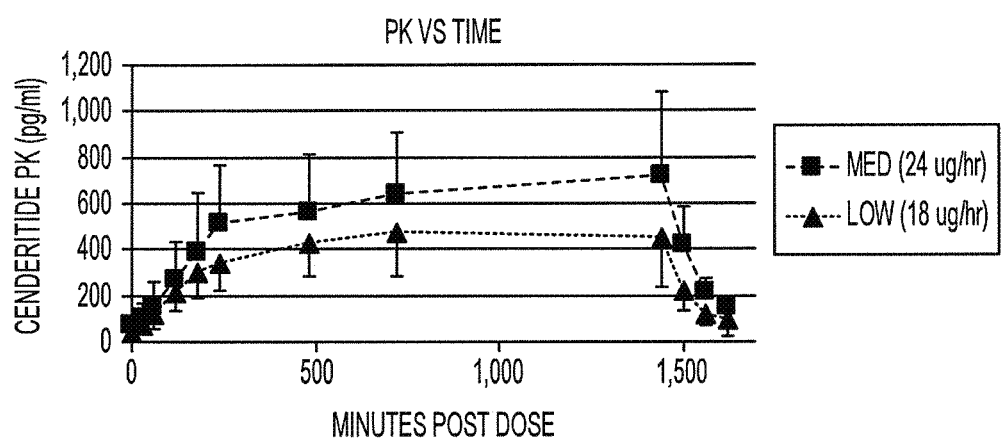
FIG. 12 is a graph depicting data from an exemplary weight-based human clinical study.

FIG. 12 shows exemplary pharmacokinetic data from the weight-based study. As depicted in FIG. 12, the concentration of CD-NP in serum vs. time after initial dosing for patients on a low dose and a medium dose.

Thus, in one aspect, the therapeutically effective blood concentrations of CD-NP was determined to be, for example, about 200 pg/mL to about 1,200 pg/mL, or about 200 pg/mL to about 1,000 pg/mL, or about 250 pg/mL to about 1,000 pg/mL, or about 300 pg/mL to about 1,000 pg/mL, or about 350 pg/mL to about 800 pg/mL. In another aspect, for many patients, this blood level can be achieved by administering, for example, about 5 µg/hr to about 50 µg/hr, or about 10 µg/hr to about 40 µg/hr, or about 15 µg/hr to about 30 µg/hr, or about 18 µg/hr to about 24 µg/hr.

In one aspect, the serum concentration of an NP, for example CD-NP, after initial administration of, for example, one of the foregoing doses, may be measured and compared to the one of the previously mentioned therapeutic ranges. In another aspect, depending on the result of the measurement, the dose of NP, for example CD-NP, may be adjusted by increasing, decreasing, or maintaining the dose in order to achieve the desired therapeutic concentration. As a non-limiting example, FIG. 13 shows the application of this method to patients in the trial. In this example, the target blood concentration was 500 pg/mL. Based on the data discussed above (in FIGS. 11 and 12), and the weight of the individual patient, an initial dose of CD-NP was estimated. Then, based on the measured blood concentration, the dose was increased or decreased by the amount specified in the table to achieve the desired concentration.

This result may be used in many practical ways. In one aspect, a dose may be sufficient to give a serum or plasma concentration between about 200 pg/mL and about 1,200 pg/mL, or between about 250 pg/mL and about 1,000 pg/mL, or between about 300 pg/mL and about 900 pg/mL, or between about 350 pg/mL and about 800 pg/mL, or between about 400 pg/mL and about 600 pg/mL, or about 500 pg/mL. In another aspect, when a patient weights more than 90 kg, then the dose may be increased in order to achieve the desired concentration. For example, for every additional about 10 to about 30 pounds, or about 20 pounds, above about 198 pounds, the dose may be increased by about 1 to about 10 µg/hr, or by about 2 to about 8 µg/hr, or by about 3 to about 6 µg/hr, or by about 4 µg/hr or by about 5 µg/hr. In yet another aspect, for every 10 to 30 pounds, or about 20 pounds, below about 198 pounds, the dose may be decreased by about 1 to about 10 µg/hr, or by about 2 to about 8 µg/hr, or by about 3 to about 6 µg/hr, or by about 4 µg/hr or by about 5 µg/hr. In still another aspect, if a measured NP concentration, for example CD-NP concentration, is less than about 200 pg/mL, or about 250 pg/mL, or about 300 pg/mL, or about 350 pg/mL, then the dosage may be increased. If a measured NP concentration, for example CD-NP concentration, is greater than about 1,200 pg/mL, about 1,000 pg/mL, or about 800 pg/mL, then the dosage may be decreased or temporarily halted.

In another aspect, a method of treating a patient with heart failure may include determining the weight of the patient, and administering an NP to the patient in a dose. In still another aspect, if the weight of the patient is more than 198 pounds, then the dose, K, in µg/hr, may be $$K=O+(D\times M)$$

and if the weight of the patient is less than 198 pounds, then the dose, L, in µg/hr, may be $$L=O-(D\times M)$$

wherein O is the dose of NP, in µg/hr, that provides a cardiac benefit to a patient weighting 198 pounds without causing hypotension, and wherein D is the value of S/20 rounded to the nearest whole number, and wherein S is the absolute value of (198−the patient's weight in pounds), and wherein M is between 1 µg/hr and 20 µg/hr. In another aspect, O may be about 5 µg/hr to about 50 µg/hr, or about 18 µg/hr to about 25 µg/hr. In a further aspect, M may be about 2 µg/hr to about 10 µg/hr, or about 2 µg/hr to about 10 µg/hr, or about 3 µg/hr to about 5 µg/hr.

Determining NP concentration, for example, CD-NP concentration, may be accomplished, in one aspect, by monitoring wherein blood is drawn at intervals, such as every 15 min, 30 min, 1 hour, 2 hours, 4 hours, 6 hours, 10 hours, 12 hours, 20 hours, 22 hours, daily, biweekly, weekly, etc.

In order to fully appreciate the results discussed here, it is important to recognize that CD-NP is only an exemplary NP. Other NP's could also be administered to achieve similar results.

Delivery of the NP may be by any known route. In one aspect, delivery may be by a route selected from the group consisting of subcutaneous, oral, parenteral, rectal, buccal, vaginal, sublingual, transdermal, intravenous, intramuscular, intraarterial, intramuscular, intraperitoneal, intraathoracic, intracoronary, intrapulmonary, and intranasal. In another aspect, a pump may be used to control the amount of NP delivered over time. In still another aspect, the absorption profile from the subcutaneous tissue compartment into the blood stream may be used to monitor NP, such as CD-NP, delivery in an appropriate dosage, such as the dosages discussed above. A feedback loop to control the external pump may be used by monitoring NP, such as CD-NP, concentration and increasing or decreasing the amount of NP administered. Such monitoring, if desired, may occur at regular intervals or at random.

In one aspect, a method of treating a patient with heart failure comprising administering an NP to the patient with a dose in the range of about 1 ng/kg/min to about 5 ng/kg/min, or about 1.25 ng/kg/min to about 3.75 ng/kg/min, or about 1.25 ng/kg/min, or about 2.5 ng/kg/min; or about 3 ng/kg/min to about 20 ng/kg/min or about 10 ng/kg/min to about 17.5 ng/kg/min, or about 5 ng/kg/min; or about 5 µg/hr and about 50 µg/hr, or about 10 µg/hr and about 40 µg/hr, or about 15 µg/hr and about 30 µg/hr, or about 18 µg/hr and about 24 µg/hr is provided. In another aspect, a method of treating a patient with heart failure comprising administering an NP to the patient in an amount sufficient to achieve a serum concentration of NP of about 200 pg/mL to about 1,200 pg/mL, or about 200 pg/mL to about 1,000 pg/mL, or about 250 pg/mL to about 1,000 pg/mL, or about 300 pg/mL to about 1,000 pg/mL, or about 350 pg/mL to about 800 pg/mL is provided.

In yet another aspect, an NP may be administered to a patient having a systolic blood pressure above about 120 mm Hg, or above about 110 mm Hg, or above about 100 mm Hg, or above about 90 mm Hg. Administering an NP to the patient may be in an amount that does not decrease the patient's systolic blood pressure below about 90 mm Hg. In still another aspect, an NP may be administered in an amount sufficient to decrease the systolic blood pressure of the patient by about 2 mm. Hg to about 10 mm Hg, or by about 5 to about 10 mm Hg.

Treating heart failure may include any type of heart failure. In one aspect, heart failure may be acute heart failure, acute decompensated heart failure, or chronic heart failure, or some combination of the above.

In an additional aspect, administration of the NP may comprise injection, oral administration, subcutaneous administration, intravenous administration, or intra-arterial administration. In a further aspect, administration of the NP may comprise subcutaneous administration. Administration of the NP may comprise an external pump.

In one aspect, an additional step may comprise monitoring the NP concentration in the serum or plasma by drawing blood from the patient and measuring the concentration of the NP in serum or plasma. Blood may be drawn at regular intervals. In another aspect, the regular intervals are selected from the group consisting of every 15 min, 30 min, 1 hour, 2 hours, 4 hours, 6 hours, 10 hours, 12 hours, 20 hours, 22 hours, daily, biweekly, and weekly. In yet another aspect, blood may be drawn at random intervals. In still another aspect, an additional step may include creating a feedback loop by increasing or decreasing the amount of NP administered after measuring the concentration of NP.

A further step of administrating an additional vasoactive medication may be included in yet another aspect. In still another aspect, the additional vasoactive medication may, for example, be administered once per day. In another aspect, the additional vasoactive medication may be, for example, selected from the group consisting of statins, beta-blockers, diuretics, ACE inhibitor, angiotensin receptor blocker, calcium channel blockers or alpha blockers, or a combination of the foregoing, furosemide, and mixtures thereof. In yet another aspect, the additional vasoactive medication may be furosemide. In another aspect, the additional vasoactive medication may be administered prior to the administration of NP, for example, to stabilize the patient. In a further aspect, the additional vasoactive medications may be administered for at least one day prior to administering an NP to the patient. In an additional aspect, the additional vasoactive medications may be administered for less than one day, or not at all, prior to administering an NP to the patient.

The NP may be administered for a time period. In one aspect, the NP may be administered without interruption for at least 24 hours. In one aspect the dose of NP during the time from about 4 hours before administration of an additional vasoactive medication until about 4 hours after administration of an additional vasoactive medication is lower than the dose of NP during the time from about 4 hours after administration of the additional medication until about four hours before administration of the additional vasoactive medication. In another aspect, the dose of NP during the time from about 2 hours before administration of an additional vasoactive medication until about 4 hours after administration of an additional vasoactive medication is lower than the dose of NP during the time from about 4 hours after administration of an additional medication until about four hours before administration of an additional vasoactive medication. In an additional aspect, administering an NP may further comprise reducing the dose of the NP about 4 hours before administration of an additional vasoactive medication. In another additional aspect, administering an NP may further comprise reducing the dose of the NP about 2 hours before administration of the additional vasoactive medication. In a further aspect, delivery of NP may also be interrupted, or terminated and then restarted, for example, in order to decrease the amount or concentration of NP in the patient's body or for some other reason. In one aspect, the term "reducing the dose" refers to lowering the amount of NP, for example CD-NP, in an amount sufficient that the risk of hypotension. In another aspect, "reducing the dose" means lowering the dose by about 1 ng/kg/min to about 10 ng/kg/min, or by about 2 ng/kg/min to about 8 ng/kg/min, or by about 4 ng/kg/min to about 6 ng/kg/min, or by about 0.5 ng/kg/min to about 1 mg/kg/min, or by about 0.25 ng/kg/min, or by about 0.5 ng/kg/min, or by about 1 ng/kg/min, or by about 1.5 ng/kg/min, or by about 2 ng/kg/min, or by about 2.5 ng/kg/min, or by about 3 ng/kg/min. In a further aspect, the NP may not be administered to the patient until about 24 hours, or about 36 hours, or about 48 hours, or about 72 hours, after admission of a patient to a hospital. In another aspect, the NP may be delivered to the patient beginning about one day after admission to a hospital and administration of the NP may continue for up to about 180 days after admission to the hospital.

The NP may be any NP. In one aspect, the NP may be elected from the group consisting of CD-NP, atrial natriuretic peptide, brain natriuretic peptide, C-type natriuretic peptide, BD-NP, and CU-NP. In another aspect, NP may be CD-NP.

This description explains and supports many novel and unobvious contributions to the art, yet the description is not intended to be limiting. Instead, the bounds of protection sought are to be limited only by the claims.

What is claimed is:

1. A method of treating a patient with heart failure comprising;
   A) administering a natriuretic peptide (NP) to the patient continuously for at least 24 hours, wherein the continuous administration comprises a first dose of the NP and a second dose of the NP; and,
   B) administering to the patient a vasoactive medication at a time point during the administration of the natriuretic peptide;
   wherein the first dose of the NP is administered to the patient from about 2 hours before the administration of the vasoactive medication up to about 4 hours after administration of the vasoactive medication; and
   wherein the second dose of the NP is administered up to about 2 hours before the administration of the vasoactive medication and about 4 hours after administration of the vasoactive medication; and,
   wherein the first dose of NP is lower than the second dose of NP.

2. The method of claim 1, wherein the heart failure is selected from the group consisting of acute heart failure, decompensated heart failure, and chronic heart failure.

3. The method of claim 1, wherein the vasoactive medication is selected from the group consisting of statins, beta-blockers, diuretics, alpha blockers, ACE inhibitor, angiotensin receptor blocker, calcium channel blockers, furosemide, and mixtures thereof.

4. The method of claim 1, wherein the NP is selected from the group consisting of CD-NP (cenderitide), atrial natriuretic peptide, brain natriuretic peptide, C-type natriuretic peptide, urodilatin, BD-NP, CU-NP, and mixtures thereof.

5. The method of claim 1, wherein the first dose of the NP is administered to the patient from about 4 hours before the administration of the vasoactive medication up to about 4 hours after administration of the vasoactive medication and wherein the second dose of the NP is administered up to about 4 hours before the administration of the vasoactive medication and about 4 hours after administration of the vasoactive medication.

6. The method of claim 1, wherein the dose of NP is sufficient to lower the systolic blood pressure of the patient by about 2 mm Hg to about 10 mm Hg.

7. The method of claim 1, wherein the NP is administered in a dose range of about 1 ng/kg/min to about 5 ng/kg/min.

8. The method of claim 1, wherein the NP is administered in a dose range of about 3 ng/kg/min to about 20 ng/kg/min.

* * * * *

```
                          SEQUENCE LISTING

<160> NUMBER OF SEQ ID NOS: 14

<210> SEQ ID NO 1
<211> LENGTH: 41
<212> TYPE: PRT
<213> ORGANISM: Artificial Sequence
<220> FEATURE:
<223> OTHER INFORMATION: Description of Artificial Sequence: Synthetic
      chimeric polypeptide

<400> SEQUENCE: 1

Ser Pro Lys Met Val Gln Gly Ser Gly Cys Phe Gly Arg Lys Met Asp
1               5                   10                  15

Arg Ile Ser Ser Ser Ser Gly Leu Gly Cys Pro Ser Leu Arg Asp Pro
            20                  25                  30

Arg Pro Asn Ala Pro Ser Thr Ser Ala
        35                  40

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      chimeric polypeptide

<400> SEQUENCE: 2

Gly Leu Ser Lys Gly Cys Phe Gly Leu Lys Asp Arg Ile Gly Ser Met
1               5                   10                  15

Ser Gly Leu Gly Cys Pro Ser Leu Arg Asp Pro Arg Pro Asn Ala Pro
            20                  25                  30

Ser Thr Ser Ala
        35

<210> SEQ ID NO 3
<211> LENGTH: 15
<212> TYPE: PRT
<213> ORGANISM: Dendroaspis angusticeps

<400> SEQUENCE: 3

Pro Ser Leu Arg Asp Pro Arg Pro Asn Ala Pro Ser Thr Ser Ala
```

<210> SEQ ID NO 4
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(35)
<223> OTHER INFORMATION: Any amino acid; This region may encompass 0-35
      residues
<220> FEATURE:
<221> NAME/KEY: MOD_RES
<222> LOCATION: (38)..(38)
<223> OTHER INFORMATION: Ser or Thr
<220> FEATURE:
<221> NAME/KEY: MOD_RES
<222> LOCATION: (39)..(39)
<223> OTHER INFORMATION: Gly, Ala, Val, Met, Leu, Nle or Ile
<220> FEATURE:
<221> NAME/KEY: MOD_RES
<222> LOCATION: (40)..(40)
<223> OTHER INFORMATION: Leu, Lys, Arg, His, Orn, Asn or Gln
<220> FEATURE:
<221> NAME/KEY: MOD_RES
<222> LOCATION: (41)..(41)
<223> OTHER INFORMATION: Asp or Glu
<220> FEATURE:
<221> NAME/KEY: MOD_RES
<222> LOCATION: (43)..(43)
<223> OTHER INFORMATION: Leu, Lys, Arg, His, Orn, Asn or Gln
<220> FEATURE:
<221> NAME/KEY: MOD_RES
<222> LOCATION: (45)..(45)
<223> OTHER INFORMATION: Gly, Ala, Val, Met, Leu, Nle or Ile
<220> FEATURE:
<221> NAME/KEY: MOD_RES
<222> LOCATION: (47)..(47)
<223> OTHER INFORMATION: Leu, Lys, Arg, His, Orn, Asn or Gln
<220> FEATURE:
<221> NAME/KEY: MOD_RES
<222> LOCATION: (48)..(48)
<223> OTHER INFORMATION: Gly, Ala, Val, Met, Leu, Nle or Ile
<220> FEATURE:
<221> NAME/KEY: MOD_RES
<222> LOCATION: (50)..(52)
<223> OTHER INFORMATION: Ser or Thr
<220> FEATURE:
<221> NAME/KEY: MOD_RES
<222> LOCATION: (53)..(53)
<223> OTHER INFORMATION: Lys, Arg, Orn, Ala, Thr, Asn or Gln

<400> SEQUENCE: 4

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Cys Pro Xaa Xaa Xaa Xaa Pro Xaa Pro Xaa Pro Xaa Xaa
         35                  40                  45

Pro Xaa Xaa Xaa Xaa
     50

<210> SEQ ID NO 5
<211> LENGTH: 28
<212> TYPE: PRT
<213> ORGANISM: Homo sapiens

<400> SEQUENCE: 5

Ser Leu Arg Arg Ser Ser Cys Phe Gly Gly Arg Met Asp Arg Ile Gly

```
                1               5                   10                  15
Ala Gln Ser Gly Leu Gly Cys Asn Ser Phe Arg Tyr
            20                  25

<210> SEQ ID NO 6
<211> LENGTH: 32
<212> TYPE: PRT
<213> ORGANISM: Homo sapiens

<400> SEQUENCE: 6

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 7
<211> LENGTH: 25
<212> TYPE: PRT
<213> ORGANISM: Homo sapiens

<400> SEQUENCE: 7

Ser Pro Lys Met Val Gln Glu Ser Gly Cys Phe Gly Arg Lys Met Asp
1               5                   10                  15

Arg Ile Ser Ser Ser Ser Gly Leu Gly
            20                  25

<210> SEQ ID NO 8
<211> LENGTH: 21
<212> TYPE: PRT
<213> ORGANISM: Homo sapiens

<400> SEQUENCE: 8

Gly Leu Ser Lys Gly Cys Phe Gly Leu Lys Leu Asp Arg Ile Gly Ser
1               5                   10                  15

Met Ser Gly Leu Gly
            20

<210> SEQ ID NO 9
<211> LENGTH: 22
<212> TYPE: PRT
<213> ORGANISM: Homo sapiens

<400> SEQUENCE: 9

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 10
<211> LENGTH: 38
<212> TYPE: PRT
<213> ORGANISM: Dendroaspis angusticeps

<400> SEQUENCE: 10

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala
        35
```

```
<210> SEQ ID NO 11
<211> LENGTH: 23
<212> TYPE: PRT
<213> ORGANISM: Dendroaspis angusticeps

<400> SEQUENCE: 11

Glu Val Lys Tyr Asp Pro Cys Phe Gly His Lys Ile Asp Arg Ile Asn
1               5                   10                  15

His Val Ser Asn Leu Gly Cys
            20

<210> SEQ ID NO 12
<211> LENGTH: 22
<212> TYPE: PRT
<213> ORGANISM: Dendroaspis angusticeps

<400> SEQUENCE: 12

Glu Val Lys Tyr Asp Pro Cys Phe Gly His Lys Ile Asp Arg Ile Asn
1               5                   10                  15

His Val Ser Asn Leu Gly
            20

<210> SEQ ID NO 13
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(35)
<223> OTHER INFORMATION: Any amino acid; This region may encompass 0-35
      residues
<220> FEATURE:
<221> NAME/KEY: MOD_RES
<222> LOCATION: (37)..(37)
<223> OTHER INFORMATION: Ser or Thr
<220> FEATURE:
<221> NAME/KEY: MOD_RES
<222> LOCATION: (38)..(38)
<223> OTHER INFORMATION: Gly, Ala, Val, Met, Leu, Norleucine or Ile
<220> FEATURE:
<221> NAME/KEY: MOD_RES
<222> LOCATION: (39)..(39)
<223> OTHER INFORMATION: Leu, Lys, Arg, His, Orn, Asn or Gln
<220> FEATURE:
<221> NAME/KEY: MOD_RES
<222> LOCATION: (40)..(40)
<223> OTHER INFORMATION: Asp or Glu
<220> FEATURE:
<221> NAME/KEY: MOD_RES
<222> LOCATION: (42)..(42)
<223> OTHER INFORMATION: Leu, Lys, Arg, His, Orn, Asn or Gln
<220> FEATURE:
<221> NAME/KEY: MOD_RES
<222> LOCATION: (44)..(44)
<223> OTHER INFORMATION: Leu, Lys, Arg, His, Orn, Asn or Gln
<220> FEATURE:
<221> NAME/KEY: MOD_RES
<222> LOCATION: (45)..(45)
<223> OTHER INFORMATION: Gly, Ala, Val, Met, Leu, Norleucine or Ile
<220> FEATURE:
<221> NAME/KEY: MOD_RES
<222> LOCATION: (47)..(49)
<223> OTHER INFORMATION: Ser or Thr
<220> FEATURE:
<221> NAME/KEY: MOD_RES
<222> LOCATION: (50)..(50)
<223> OTHER INFORMATION: Lys, Arg, Orn, Ala, Thr, Asn or Gln
<220> FEATURE:
<221> NAME/KEY: MOD_RES
<222> LOCATION: (51)..(85)
```

<223> OTHER INFORMATION: Any amino acid; This region may encompass 0-35
      residues
<220> FEATURE:
<223> OTHER INFORMATION: See specification as filed for detailed
      description of substitutions and preferred embodiments

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Pro Xaa Xaa Xaa Xaa Pro Xaa Pro Xaa Xaa Pro Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
            85

<210> SEQ ID NO 14
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(35)
<223> OTHER INFORMATION: Any amino acid; This region may encompass 0-35
      residues
<220> FEATURE:
<221> NAME/KEY: MOD_RES
<222> LOCATION: (37)..(37)
<223> OTHER INFORMATION: Ser or Thr
<220> FEATURE:
<221> NAME/KEY: MOD_RES
<222> LOCATION: (38)..(38)
<223> OTHER INFORMATION: Gly, Ala, Val, Met, Leu, Norleucine or Ile
<220> FEATURE:
<221> NAME/KEY: MOD_RES
<222> LOCATION: (39)..(39)
<223> OTHER INFORMATION: Leu, Lys, Arg, His, Orn, Asn or Gln
<220> FEATURE:
<221> NAME/KEY: MOD_RES
<222> LOCATION: (40)..(40)
<223> OTHER INFORMATION: Asp or Glu
<220> FEATURE:
<221> NAME/KEY: MOD_RES
<222> LOCATION: (42)..(42)
<223> OTHER INFORMATION: Leu, Lys, Arg, His, Orn, Asn or Gln
<220> FEATURE:
<221> NAME/KEY: MOD_RES
<222> LOCATION: (44)..(44)
<223> OTHER INFORMATION: Leu, Lys, Arg, His, Orn, Asn or Gln
<220> FEATURE:
<221> NAME/KEY: MOD_RES
<222> LOCATION: (45)..(45)
<223> OTHER INFORMATION: Gly, Ala, Val, Met, Leu, Norleucine or Ile
<220> FEATURE:
<221> NAME/KEY: MOD_RES
<222> LOCATION: (47)..(49)
<223> OTHER INFORMATION: Ser or Thr
<220> FEATURE:
<221> NAME/KEY: MOD_RES
<222> LOCATION: (50)..(50)
<223> OTHER INFORMATION: Lys, Arg, Orn, Ala, Thr, Asn or Gln
<220> FEATURE:
<221> NAME/KEY: MOD_RES
<222> LOCATION: (51)..(85)
<223> OTHER INFORMATION: Any amino acid; This region may encompass 0-35

```
        residues
<220> FEATURE:
<223> OTHER INFORMATION: See specification as filed for detailed
      description of substitutions and preferred embodiments

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Pro Xaa Xaa Xaa Xaa Pro Xaa Pro Xaa Xaa Pro Xaa Xaa
        35                  40              45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa
                85
```